(12) United States Patent
Balzarini (10) Patent No.: US 10,194,925 B2
(45) Date of Patent: Feb. 5, 2019

(54) MEDICAL TOOL SYSTEM (71) Applicant: WALDEMAR LINK GmbH & Co. KG, Hamburg (DE)

(72) Inventor: Amos Balzarini, Norderstedt (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 601 days.

(21) Appl. No.: 14/771,083

(22) PCT Filed: Jan. 16, 2014

(86) PCT No.: PCT/EP2014/050797
§ 371 (c)(1),
(2) Date: Aug. 27, 2015

(87) PCT Pub. No.: WO2014/135293
PCT Pub. Date: Sep. 12, 2014

(65) Prior Publication Data
US 2016/0008012 A1  Jan. 14, 2016

(30) Foreign Application Priority Data

Mar. 5, 2013  (EP) ..................................... 13157855

(51) Int. Cl.
*A61B 17/00* (2006.01)
*A61B 17/16* (2006.01)
(Continued)

(52) U.S. Cl.
CPC ........ *A61B 17/1675* (2013.01); *A61B 17/162* (2013.01); *A61B 17/1764* (2013.01);
(Continued)

(58) Field of Classification Search
CPC combination set(s) only.
See application file for complete search history.

(56) References Cited

U.S. PATENT DOCUMENTS 5,653,714 A     8/1997  Dietz et al.
2006/0189989 A1  8/2006  Bert
(Continued)

FOREIGN PATENT DOCUMENTS

DE     19501550     7/1996
DE     20303643     8/2003
(Continued)

*Primary Examiner* — Sameh Boles
(74) *Attorney, Agent, or Firm* — Sand & Sebolt (57) ABSTRACT

A medical tool system for providing a trapezoidal recess in a joint surface of a bone, including a milling tool rotatable about a tool axis and having milling edges active on the circumferential side and milling edges that are active at an axial end with respect to the tool axis, and a template part fixable to the joint surface for guiding the milling too. A stop limits a penetration depth of the milling tool. The template part has a base element with a slide guide and a slide which can be moved in the slide guide between two end stops along a guide path lying on a guide plane. A guide channel which runs diagonally to the guide plane and leads to a milling tool receiving area directed transversely to the tool axis is formed in the slide such that the milling tool can rotate freely about the tool axis.

11 Claims, 6 Drawing Sheets

(51) Int. Cl.
*A61B 17/17* (2006.01)
*A61B 90/00* (2016.01)
(52) U.S. Cl.
CPC ...... *A61B 90/03* (2016.02); *A61B 2017/1602* (2013.01); *A61B 2090/034* (2016.02)

(56) References Cited

U.S. PATENT DOCUMENTS

2008/0183172 A1* 7/2008 Fritzinger .......... A61B 17/1728
606/71
2014/0046331 A1* 2/2014 Amos .................. A61B 17/155
606/80

FOREIGN PATENT DOCUMENTS

| | | |
|---|---|---|
| DE | 60320485 | 5/2009 |
| DE | 602004013383 | 6/2009 |
| EP | 2514372 | 10/2012 |
| WO | 2006127283 | 11/2006 |

* cited by examiner

MEDICAL TOOL SYSTEM

TECHNICAL FIELD

The present invention relates to a medical tool system for preparing a trapezoidal recess in a joint surface of a bone with a reamer that can be driven to rotate about a tool axis, having reaming blades which act on the perimeter, and having reaming blades which act at an axial end with respect to the tool axis, and having a template part which can be fixed to the joint surface for guiding the reamer, wherein a stop is provided that limits the penetration depth of the reamer.

BACKGROUND OF THE INVENTION

It has been conventional for a great while in the field of surgical orthopedics to entirely or partially replace joints that are worn, sclerotic or damaged by other diseases with prosthetic implants. In particular, the replacement of knee joints with corresponding implants, as well as the setting of artificial hip joints or hip joint parts, is presently part of the standard surgical repertoire in surgical orthopedics. Depending on the severity of the joint defect, highly different techniques and surgical methods have been developed in the past. In addition to total replacement prostheses where the joint surfaces and neighboring bone section are completely replaced with artificially formed implant parts, e.g. for a worn knee joint both in the region of the femur as well as in the region of the tibia, techniques and systems are now common in which worn joint surfaces are only partially replaced while largely retaining the natural bone substance. For example, there are implant systems in which only one of the two condyles of the tibia-side joint surface is replaced in knee joints with a partial prosthesis, the other condyle of course being left, and an artificial contact surface of the joint is only applied on the side of the part of the femur part opposite the replaced condyle surface provided with the artificial implant.

Such partial prostheses are frequently anchored in the bone with bar-shaped or otherwise-shaped extensions, such as with so-called fins. These fins, which are slightly oversized, are pressed into a corresponding recess or hollowed-out groove created in the bone material, and the fins are frequently formed with a trapezoidal cross-section. Such fastening mechanisms can however be used for other implants that are to be fixed in the bone as well as for total replacement prostheses, and not just for partial implants.

However when sparing partial replacement prostheses are implanted, care is taken to retain as much of the soft tissues, in particular the ligaments, surrounding the joint region possible and leave said tissues free of damage. Correspondingly, separation of the natural joint is minimized to reduce the stress and promote regeneration and the healing process at this location in order to retain as much of the joint stability provided by the natural soft tissue as possible. Consequently, related tools systems with which the structures must be created in damaged bones in which prosthetic parts are fixed must be designed such that said tool systems can also be inserted into small gaps and nonetheless function with sufficient precision.

Whereas earlier it was frequently left to the dexterity and manual skill of the surgeon to prepare the joint surfaces of the bones involved for the replacement of worn joint regions in a freehand manner, increasingly, technical tools have gained acceptance in the interim to render the surgeon's handwork easier, and to ensure that the required structures are securely and precisely arranged and formed.

Accordingly, various tool systems are known for removing bone material in which templates interact with reaming in order to create recesses of a given shape and depth.

Such a tool system that is used to ream out recesses of a predetermined contour is disclosed in DE 603 20 485 T2. A reamer having a reaming head provided with a radius is inserted into a guide slot in a plate-shaped template and clears out a cassette-like free space due to the provided guidance. Similarly, a system with a template guide and reamer is disclosed in DE 195 01 550 A1.

DE 60 2004 013 383 T2 discloses a system with a template and a reamer guided therein for preparing the condyle surfaces of a knee prosthesis. In the device depicted therein, the rotating shaft of the reamer runs substantially vertically upward and requires a great deal of free space so that, during surgery and the preparation phase, the femur part of the knee must be moved back a great deal, which cannot be reconciled with the aim of retaining the soft tissues of the joint, in particular the ligaments, and in this case, the cruciate ligaments in particular.

Furthermore, an implant system marketed by the U.S. company Stryker Corporation under the brand name of EIUS™ is known in the market for partial replacement of the knee, having a condyle surface to be replaced on one side and a joint surface implant which is also affixed to one side of the femur. A preparation tool is provided for this implant system in which a trapezoidal recess is formed in the condyle surface of the tibia to be treated. To accomplish this, there is a template part with a plate element that has a tubular section which is securely connected to the plate element and has a rectangular cross section which forms a tool tunnel running at an angle of approximately 45° relative to the plane of the plate. To form a trapezoidal recess, a drilling template is first inserted into this tunnel, and weakening holes are introduced into the bone material. The drilling insert is then removed, and the bone, perforated in this manner, is fully cleared with a clearing chisel, which is also introduced through the tunnel to form the recess into which the fin of the condyle implant is introduced. On one hand, the tool system has many parts, and the associated method for forming the recess is complicated. Using different tools, first the drill holes must first be introduced with different tools, and then final clearing of the recess must then be performed. This procedure takes up valuable time during the surgery and also leads to numerous parts and instruments having to be cleaned and disinfected following the operation.

DESCRIPTION OF THE INVENTION

The object of the invention is to offer a simplification and create an optimized medical tool system by means of which trapezoidal recesses can be created in a joint surface of a bone, even under spatially restricted conditions. In particular, this tool system is suitable for creating such a trapezoidal recess in a condyle surface of the tibia part of the knee joint, for example in preparation for setting a partial replacement prosthesis in this region.

This object is achieved according to the invention by a medical tool system with a reamer that can be driven to rotate about a tool axis, having reaming blades which act on the perimeter, and having reaming blades which act at an axial end with respect to the tool axis, and having a template part which can be fixed to the joint surface for guiding the reamer, wherein a stop is provided that limits the penetration depth of the reamer and wherein the template part has a base element with a carriage guide, and a carriage that can move in the carriage guide between two end stops along a guide path lying within a guide plane, wherein a guide channel, running oblique to the guide plane to accommodate the reamer guided transversely to the tool axis, is formed in the carriage such that the reamer can rotate freely about the tool axis. Advantageous developments of this novel tool system include that the base element is plate-shaped and flat; and the carriage guide is formed in the base element by a straight longitudinal slot in which a guide extension of the carriage is received. The guide channel is inclined relative to the guide plane at an angle of 30° to 60°, in particular at an angle of 40° to 50°, and particularly preferably at an angle of 45°. The reaming blades acting at the axial end with respect to the tool axis ream out a surface while reaming which is substantially flat and perpendicular to the tool axis. The guide channel is disposed in a tubular section of the carriage which has an upper edge, and the reamer has a collar which projects transversely to the tool axis, wherein the edge and the collar together form the stop. The carriage and base element of the template part are releasably connected to each other. The tool system also includes pinholes in the base element and a handle section on the base element.

In accordance with known, comparable tool systems, the novel medical tool system for preparing a trapezoidal recess in a joint surface of a bone according to the invention has a reamer which can be driven to rotate about a tool axis and has reaming blades which act on the perimeter, and furthermore has reaming blades which act at an axial end with reference to the tool axis. In addition and also corresponding to previously known, comparable tool systems, it has a template part which can be fixed to the joint surface for guiding the reamer, and a stop is provided that limits the penetration depth of the reamer is provided.

What is special about the tool system according to the invention is that the template part has a base element with a carriage guide, and furthermore a carriage that can move in the carriage guide between two end stops along a guide path lying within a guide plane. Furthermore, according to the invention, a guide channel is formed in the carriage to receive the reamer. The received reamer received in this guide channel is then guided transversely to the tool axis, i.e., it cannot move in a direction transverse to this tool axis relative to the guide channel. Within this guide channel, the reamer can, however, rotate freely about the tool axis and move in an axial direction.

The tool system according to the invention can be used to form a trapezoidal recess in a condyle surface of the tibial part of a knee joint, for example, and is particularly suitable for this. In preparing the condyle surface for setting a prosthetic implant, the condyle surface is first prepared with a cut running transversely to the longitudinal axis of the tibia, and a separating cut transverse to this cut is prepared in order to produce a flat plateau at that location. A trapezoidal recess is introduced in this flat plateau, into which an anchoring projection, typically designated a fin, of a corresponding implant can be pressed. After preparation of the flat plateau, the base element of the template part of the tool system according to the invention is placed, and in particular secured, on the surface thus created. The carriage, which can move back and forth on the base element in the carriage guide between the two end stops, can now slide back and forth between these end stops, and accordingly, space is also available for minimally invasive surgical techniques. The reamer is introduced through the guide channel in the carriage and set in rotation. The reamer cuts into the bone surface at the predetermined angle of the oblique position of the guide channel relative to the guide plane. A corresponding recess is reamed out by moving the carriage back and forth and the reamer forward and backward in the guide channel up to, at most, the stop while the reamer is simultaneously rotating. The stop prevents the reamer from penetrating too deeply into the bone and sets the depth of the recess. Since the reamer has reaming blades which act in the peripheral direction as well as in the direction of the axial end, it reams the recess smooth and clean at a flank formed by the axial end of the reamer which is created when the carriage is moved, at most, in an advancing direction of the reamer in the carriage guide up to the end stop, and the reamer is introduced into the guide channel up to the stop. The oblique position of the guide channel in the carriage exists in particular so that a part facing away from the guide plane lies at a front end of the carriage, i.e. the end of the carriage that is to be positioned proximally during surgery. This produces a type of wedge shape of the guide channel in the carriage with the shorter height being toward the distal end of the natural knee joint so that the required working height is lowest at that location, and the other parts of the knee joint which are typically moved there during surgery, i.e., the femur with the soft tissues, in particular the ligaments, do not interfere with the process, and substance can be retained accordingly while working.

In contrast, for example, to the known system of the vendor, Stryker Corporation, the entire clearing of the recess is achieved with a single tool, i.e., the reamer, and preparatory work with bone drills and subsequent final clearing with a chisel are unnecessary.

The base element is advantageously designed plate-shaped and flat, as provided according to a further development of the invention. With the plate-shaped and flat design, the base element is particularly well-adapted to the typically flat, prepared surface following the condyle cut. In addition, a particularly low overall height is achieved with a plate-shaped base element, which is advantageous with regard to the aforementioned goals of minimal interference with the natural joint structure. The thickness of the plate-shaped base element is generally selected to enable sufficiently stable and precise guidance of the carriage with a minimum thickness thereof.

Advantageously, the carriage guide of the tool system according to the invention can be formed in the base element by means of a straight longitudinal slot in which the guide extension of the guide carriage is received. Such a carriage guide is technically simple to realize and easy to use; on the other hand, it is the ideal guide for forming a straight recess having a trapezoidal cross-section. The trapezoidal shape of the recess arises due to the oblique position of the axis of the reamer relative to the base of the recess, and also relative to the flat surface remaining after the condyle cut. A front boundary surface is consequently oblique to this axial position; a rear boundary surface is formed at an angle by the reaming blades acting at the axial end, in particular when, during reaming, the reaming blades acting at the axial end with respect to the tool axis, ream out a surface, which is substantially flat and perpendicular to the axis of rotation. In the simplest case, the reamer can have a cylindrical outer contour with a free axial end that runs substantially perpendicular to the tool axis, and has reaming edges or blades along the circumference and on the front end.

The guide channel is advantageously inclined relative to the guide plane at an angle of 30° to 60°, in particular at an angle of 40° to 50°, wherein an inclination at an angle of 45° is particularly preferred. The cited angular ranges yield oblique positions of the reamer which no longer enter into the actual joint region in an interfering and space-consuming manner, also taking into consideration the long reaming shaft to be connected to the reaming drive, i.e., the region where the bone that is set aside during surgery and that is the partner of the bone with the joint surface to be processed is located, as well as the region where the soft tissues of the joints are located. In this regard, the solution according to the invention strongly differs from that of DE 60 2004 013 383 T2 which requires a significant amount of space there, given the vertical guidance of the reamer shaft.

An angle of 45° is particularly preferable in this regard since this creates a trapezoidal recess with lateral, oblique boundary surfaces, which are both at an angle of 45°. The first lateral surface follows the incline of the tool axis relative to the guide plane; the second lateral surface is correspondingly inclined at a 90° angle, i.e., 45° relative to the guide surface in the other alignment. This 90° difference is caused by the design of the reamer which has reamer blades at its axial end which act to create a surface section running vertical to the tool axis.

According to another advantageous development of the invention, the guide channel can be disposed in a tubular section of the carriage which has an upper edge. In this development, the reamer has a collar which projects transversely to the axis of rotation. The edge of the tubular section and the collar together form the stop which limits the penetration depth of the reamer into the guide channel, and hence the working depth in the bone material, in order to thereby determine and precisely maintain the depth of the trapezoidal recess.

The carriage and base element can be advantageously releasably connected to each other in order to simplify cleaning and sterilization of the template part. In particular, this makes it unnecessary to clean and sterilize gaps which may otherwise exist in the region of the movable connection.

The base element of the template part can advantageously have pinholes in order to fix the template part on the bone to be processed, and hence to maintain the position of the recess to be introduced into the bone with the assistance of the template part and the reamer interacting therewith. Such pinholes are passages through which fastening pins or screws, so-called pushpins or screw pins, can be inserted into drill holes previously introduced into the bone. Such pins are widely known and are used to a great extent in orthopedic surgery to fix auxiliary devices and tool guides.

A handle section can also be formed on the base element for easy positioning when correctly placing the template part.

From the above description, it is clear that a trapezoidal recess can be easily introduced very precisely and quickly in a joint surface of a bone using the tool system according to the invention without needing to use a wide range of tools. Due to the oblique position of the guide channel relative to the guide plane, this can be done even under spatially restricted conditions that predominate in particular when the surgery is to be largely nondestructive, in particular while retaining the soft tissues of the joint, such as the cruciate ligaments of a knee joint to be treated.

BRIEF DESCRIPTION OF THE DRAWINGS

Additional advantages and features of the invention arise from are found in the subsequent description of an exemplary embodiment with reference to the accompanying figures. In the following.

WAYS TO IMPLEMENT THE INVENTION

The figures show a possible exemplary embodiment of a tool system according to the invention which will be further described below with reference to these figures.

Figure 1:
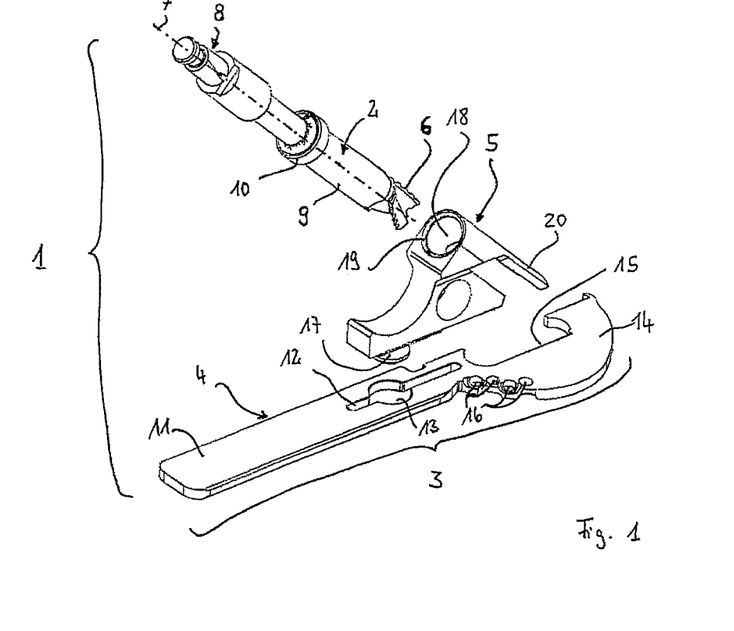
FIG. 1 shows an exemplary embodiment of a three-dimensional exploded view of a medical tool system according to the invention for preparing a recess having a trapezoidal cross-section in a joint surface of a bone.

The tool system according to the invention is generally designated as 1 and comprises a rotationally driven reamer 2 and a template part 3. The template part 3, for its part, is designed in two parts with a base element 4 and a carriage 5 which can be fixed on the base element 4 and can travel in a direction of travel between two stop points.

The reamer 2 is designed such that it extends in an axial direction and has reaming blades 6 on a clearing end which, on the one hand, act on the circumference and on the other hand, at its front end of the reamer, also exhibit a surface clearing effect along a clearing surface which is substantially perpendicular to the longitudinal axis 7 of the reamer 2. At the end opposite the clearing end having the reaming blades 6, the reamer 2 has a coupling connection 8 for connecting to a rotational drive. Proceeding from the removing end with the reaming blades 6 toward the end with the coupling connection 8, a cylindrical section 9 extends up to an annular peripheral thickening 10 which has a greater diameter than the diameter of the cylindrical section 9.

As already described, the template part 3 is designed in two parts and consists of a base element 4 and a carriage 5 which can be releasably fixed to this base element 4 and which is guided in a carriage guide in a fixed state. The base element 4 is designed in the shape of the plate having a grip section 11 which can be gripped and held during use. Furthermore, said base element has a longitudinal slot 12 which opens at one position with a circular hole 13 having a diameter greater than the slot width. A tool passage cutout 15 is formed in an approximately semicircular contact section 14. Furthermore, approximately four pinholes 16 are arranged in the base element 4.

On its bottom side, the carriage 5 has a guide pin which terminates with a circular retaining plate 17. The diameter of this circular retaining plate 17 approximately corresponds to the diameter of the circular hole 13 so that the retaining plate 17 can be guided through the circular hole 13 in order to introduce the guide pin of the carriage into the longitudinal slot 12 in order to guide the carriage 5 longitudinally and lock it in all positions with the exception of the position at which the retaining plate 17 and circular hole 13 are precisely flush.

A guide channel 18 is created in the carriage 5, which channel is formed by a guide opening having a peripheral edge 19 and a subsequent channel having a peripheral, cylindrical wall. The diameter of the guide channel 18 substantially corresponds to the diameter of the cylindrical section 9 so that the reamer 2, with its removing end equipped with reaming blades 6 at the front, can be inserted into the guide channel 18 and rotate laterally while being securely guided. The guide channel 18 is aligned such that it lies oblique to carriage guide axis formed by the longitudinal extension of the longitudinal slot 12, in particular at an angle of approximately 45°. Arranged at a front side of the carriage 5, facing away from the grip section 11, is a shield section 20 in an extension of the guide channel 18 which serves to cover the reaming blades 6 in this region when using the tool system 1, and in particular to prevent undesired injury to surrounding tissue or bone sections to be retained while introducing the reamer 2 with its removing end at the front into the guide channel 18.

Figure 2:
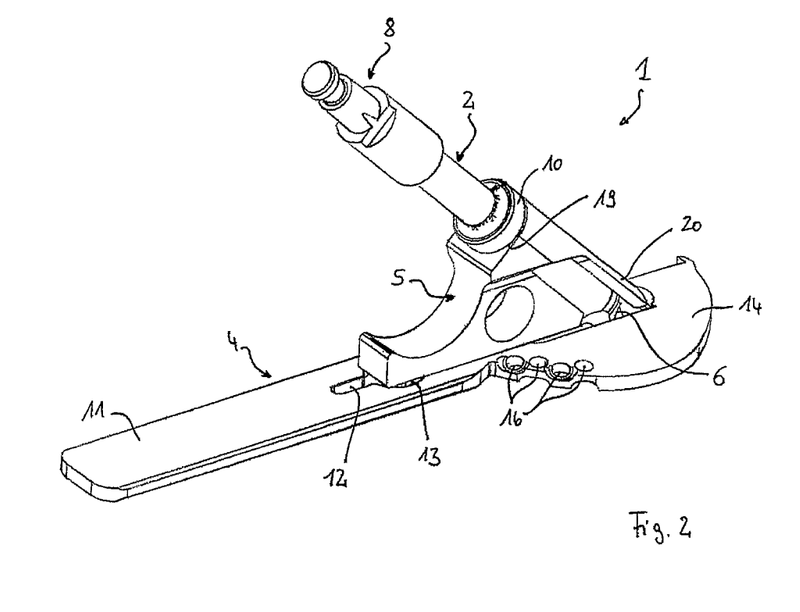
FIG. 2 shows a medical tool system from FIG. 1 in an assembled state.

FIG. 2 depicts an exploded view of the tool system 1 shown in FIG. 1 in a comparative perspective in an assembled state. It can be distinctly seen that the peripheral groove 19 in the guide opening in the guide channel 18, together with the annular thickening 10 on the reamer 2, form a stop which limits the penetration depth of the removing end of the reamer 2 equipped with the reaming blades 6.

Figure 3:
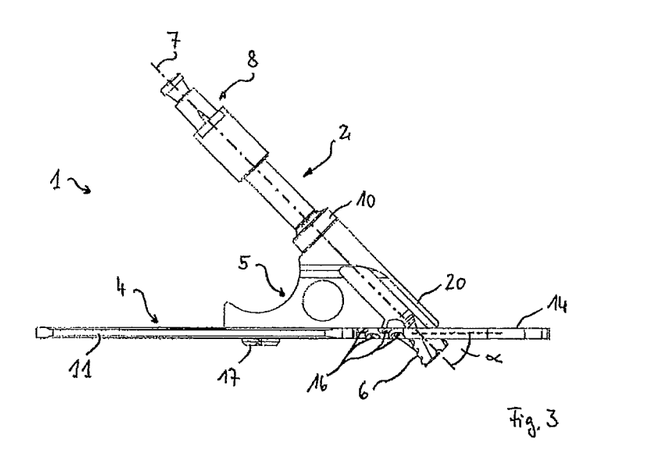
FIG. 3 shows a side view of the the tool system from FIG. 2 with a carriage located in a rear end position.

FIG. 3 shows a side view depicting how the removing end of the reamer 2, which is inserted the maximum depth into the guide channel, projects with the reaming blades 6 up to a working depth beyond a plane of the base element 4 designed as a plate when the carriage 5 is located in a stop position limited by the rear end of the longitudinal slot 12. The angle α, which in this case is preferably 45°, can also be discerned here between the plate plane and the longitudinal axis 7 of the reamer 2.

Figure 4:
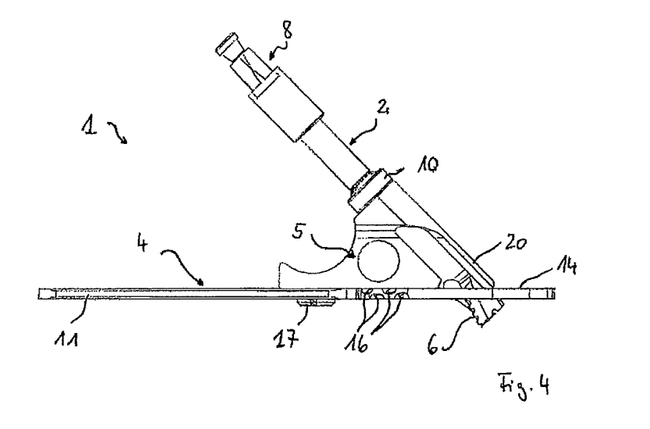
FIG. 4 shows the tool system from FIG. 1 in a view comparable with FIG. 3 with a carriage located in a front end position.

FIG. 4 shows the medical tool system 1, in a position comparable with FIG. 3, in a position in which the carriage 5 is located in a front, stop position, which is established by the front-end of the longitudinal slot 12.

Figure 5:
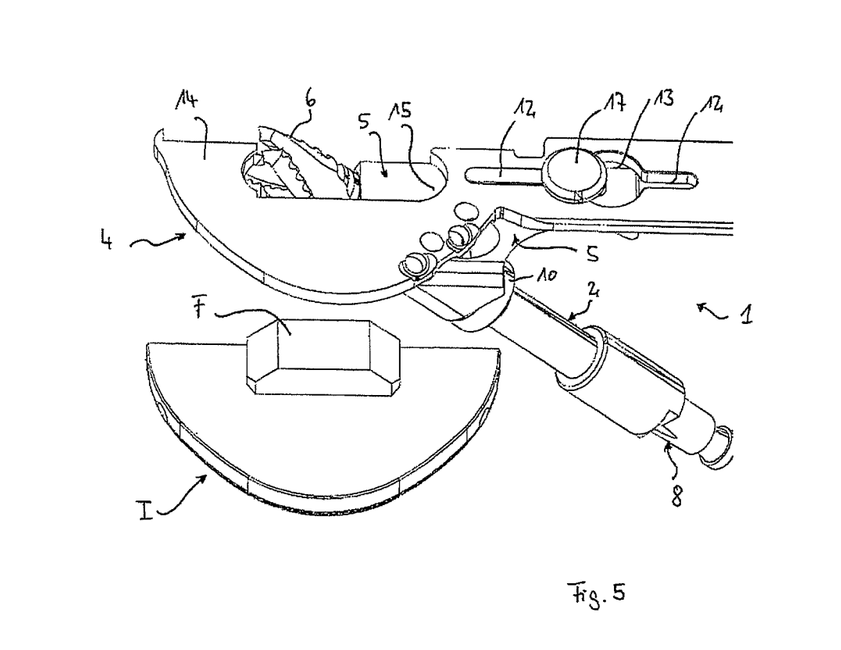
FIG. 5 shows a medical tool system from FIG. 1 in a view from below, and, in comparison, the bottom side of a medical implant part with an anchoring fin having a trapezoidal cross section.

FIG. 5 shows the tool system 1 in a view of the bottom in a depiction from above. It can be easily discerned how the reamer 2, with the removing end equipped with the reaming blades 6, extends through the tool passage cutout 15 in the contact section 14 of the base element 4. The guidance of the carriage 5 by the interaction of the pins held in the longitudinal slot 12 with the retaining plate 17 is also easily discerned. The same figure shows an implant part I with a fin F in a lower depiction, also in a view from below, the fin being formed with a trapezoidal cross-section and forming an anchoring element for the implant part I to fix the same in a bone. The medical tool system 1 serves to create a recess in a bone substantially corresponding to the shape of the fin F, or to clear the recess in the bone material, respectively.

Figure 6:
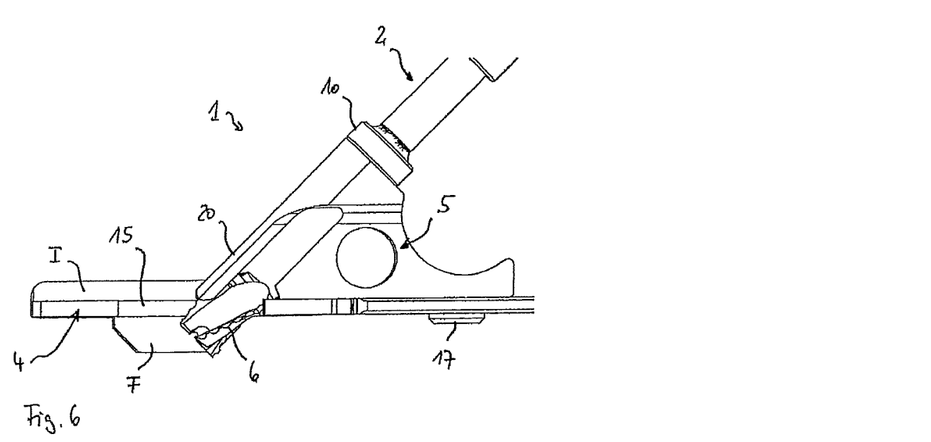
FIG. 6 shows an overlapping comparative representation from the side of the medical tool system from FIG. 1 with a fin of an implant part to the rear that has a trapezoidal cross-section, the carriage being located in its rear stop position in this figure.
Figure 7:
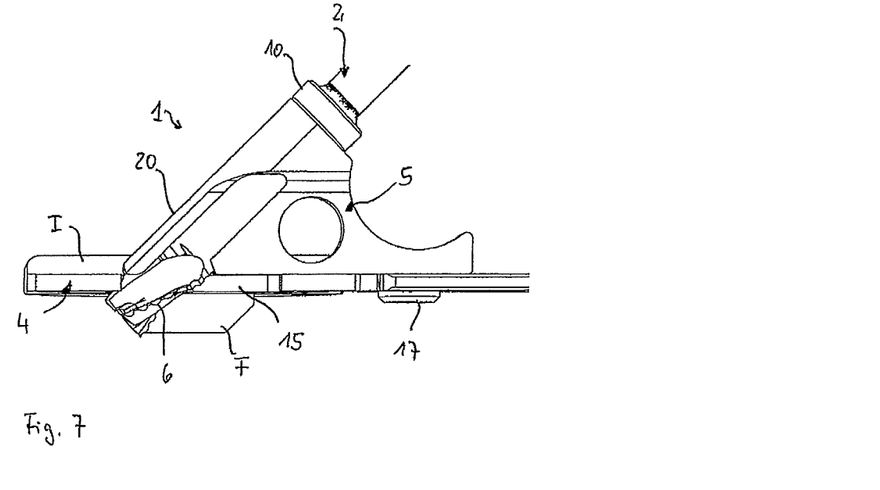
FIG. 7 shows the medical tool system in a view comparable with FIG. 6 with the carriage in a front stop position, again overlapping with the view of the fin.

In this regard, FIGS. 6 and 7 once again clearly illustrate how this is accomplished in practice. In a side view from the side opposite the views in FIGS. 3 and 4, i.e., in this case looking at the tool passage cutout 15 open at the side, FIGS. 6 and 7 show the tool system 1 in a partial view depicted in front of the implant part I with the fin F. FIG. 6 shows the system with the carriage 5 in a maximally retracted position. It can be seen how the circumferential path of the removing end of the reamer 2 equipped with reaming blades 6, depicted at the bottom right in the figure, substantially follows the path of the fin F in this region. In the position shown in FIG. 7, the front surface of the clearing end, at which the reaming blades 6 also act abrasively, covers the flank of the fin F substantially perpendicular to the longitudinal axis of the reamer 2. Accordingly, it is fully understandable that by introducing the reamer through the guide channel into a position at which the carriage is most retracted, a cut can be created which extends to the base of the recess to be introduced corresponding to the bottom edge of the fin F. By pulling or moving the carriage 5 back and forth, a recess is cleared having a trapezoidal cross-section and an outer contour corresponding to the fin F.

Figure 8:
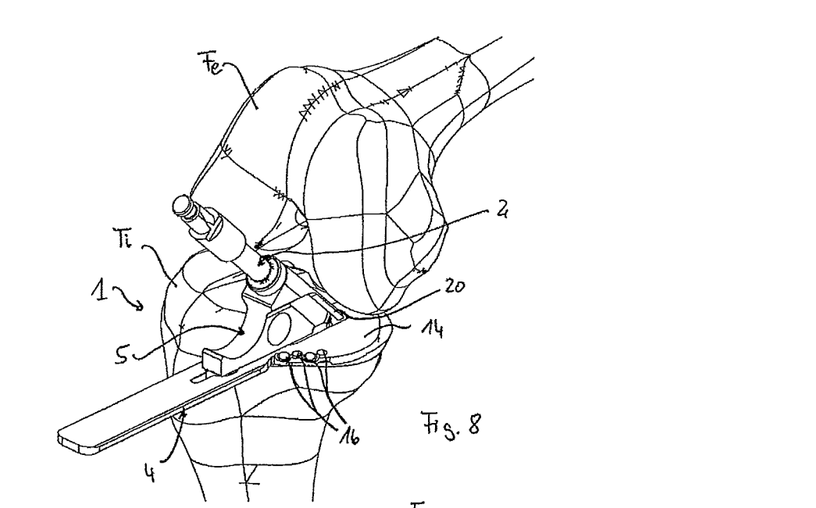
FIG. 8 shows a perspective view of the medical tool system in use for preparing a recess having a trapezoidal cross section on a tibia plateau of a knee joint that has been prepared beforehand.
Figure 9:
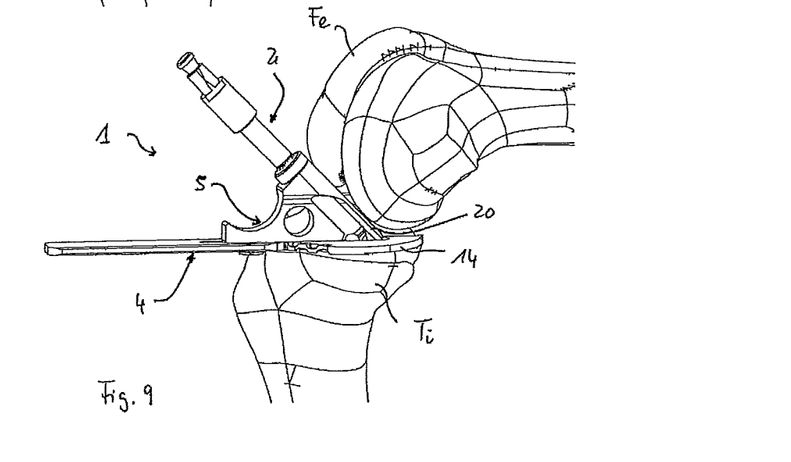
FIG. 9 shows the situation and arrangement shown in FIG. 8 from a different perspective, a side view in this case.

Such an insert in practice is shown from two different views in FIGS. 8 and 9. They show how the tool system 1, provided in this instance for forming a corresponding recess to anchor an implant part for a knee partial replacement prosthesis, is used. The distal end of the femur Fe and the proximal end of the tibia Ti can be seen here. On one side of the proximal end of the tibia Ti, a plateau has been created previously by a horizontal cut, on which the base part 4 of the tool system 1 is placed with its contact section 14. The base part 4 is first aligned corresponding to the position of the recess to be introduced, and is fixed in this position by introducing one or more retaining pins (not shown) through one or more of the pinholes 16 into the bone. The carriage 5 is then mounted and fixed on the base element 4 in the longitudinal slot for longitudinal guidance, the reamer 2 is guided through the guide channel into the carriage 5, and the recess having a trapezoidal cross-section is precisely created by moving the carriage 5 back-and-forth with the reamer 2 inserted up to the stop. In FIGS. 8 and 9, it is also quite easily discernible that the axis of the reamer 2 definitely extends out of the region in which a particularly small gap is left between the tibia Ti and femur Fe due to the angled position of the guide channel. Accordingly, the femur Fe does not have to be separated as far from the tibia Ti for surgery as is otherwise conventional, which enables surgery that spares soft tissue while retaining the natural ligaments, in particular the cruciate ligaments as well. Given the wedge shape of the carriage in its region facing the contact section 14, the required space at this location is particularly slight. It can also be seen that the shield section 20 prevents the femur Fe or neighboring soft tissues from being accidentally damaged at this location while working with the reamer 2 since the shield section 20 there reliably shields the clearing end of the reamer 2 with the reaming blades.

The depicted exemplary embodiment is not to be understood as being restrictive but rather merely illustrating one of many possible realizations of the medical tool system according to the invention.

LIST OF REFERENCE NUMBERS

1. Medical Tool System
2. Reamer
3. Template part
4. Base element
5. Carriage
6. Reaming blades
7. Longitudinal axis 8. Coupling connections
9. Cylindrical section
10. Annular thickening
11. Grip section
12. Longitudinal slot
13. Circular hole
14. Contact section
15. Tool passage cutout
16. Pinhole
17. Retaining plate
18. Guide channel
19. Circumferential edge
20. Shield section
α Angle
F Fin
Fe Femur
I Implant part
Ti Tibia

The invention claimed is:

1. A medical tool system for preparing a recess having a trapezoidal cross-section in a joint surface of a bone said tool system comprising: a reamer that is drivable to rotate about a tool axis, said reamer having reaming blades which act on a perimeter, and having reaming blades which act at an axial end with respect to the tool axis, and having a template part which is fixable to the joint surface for guiding the reamer, wherein a stop is provided that limits a penetration depth of the reamer, and wherein the template part has a base element with a carriage guide and a carriage that is movable in the carriage guide while the carriage is connected to the carriage guide; and wherein the carriage is movable relative to the carriage guide between two end stops along a guide path lying within a guide plane, wherein a guide channel, running oblique to the guide plane to accommodate the reamer guided transversely to the tool axis, is formed in the carriage such that the reamer is freely rotatable about the tool axis.

2. The tool system according to claim 1, wherein the base element is plate-shaped and flat.

3. The tool system according to claim 1, wherein the carriage guide is formed in the base element by a straight longitudinal slot in which a guide extension of the carriage is received.

4. The tool system according to claim 1, wherein the guide channel is inclined relative to the guide plane at an angle of 30° to 60°.

5. The tool system according to claim 4, wherein the guide channel is inclined relative to the guide plane at an angle of 40° to 50°.

6. The tool system according to claim 5, wherein the guide channel is inclined relative to the guide plane at an angle of 45°.

7. The tool system according to claim 1, wherein the reaming blades acting at the axial end with respect to the tool axis ream out a surface while reaming which is substantially flat and perpendicular to the tool axis.

8. The tool system according to claim 1, wherein the guide channel is disposed in a tubular section of the carriage which has an upper edge, and wherein the reamer has a collar which projects transversely to the tool axis, and wherein the upper edge and the collar together form the stop.

9. The tool system according to claim 1, wherein the carriage and base element of the template part are releasably connected to each other.

10. The tool system according claim 1, further comprising pinholes defined in the base element.

11. The tool system according to claim 1, further comprising a handle section provided on the base element.

* * * * *